United States Patent [19]

Kumadaki et al.

[11] Patent Number: 4,916,221
[45] Date of Patent: Apr. 10, 1990

[54] FLUORINE-CONTAINING PROTOPORPHYRIN DERIVATIVES AND THEIR SALTS

[75] Inventors: Itsumaro Kumadaki, Hirakata; Akira Ando, Yawata; Haruo Sato, Chiba, all of Japan

[73] Assignee: Sato Pharmaceutical Research Institute Ltd., Tokyo, Japan

[21] Appl. No.: 267,327

[22] Filed: Nov. 4, 1988

[30] Foreign Application Priority Data

Nov. 9, 1987 [JP] Japan .................. 62-282344

[51] Int. Cl.$^4$ .................. C07D 487/22
[52] U.S. Cl. .................. 540/145
[58] Field of Search .................. 540/145

[56] References Cited

PUBLICATIONS

H. H. Imhoffen, et al. Justus Liebig's Ann. Chemie, 730, 173, (1969).

*Primary Examiner*—Mukund J. Shah
*Assistant Examiner*—E. C. Ward
*Attorney, Agent, or Firm*—Oblon, Spivak, McClelland, Maier & Neustadt

[57] ABSTRACT

Disclosed herein is a fluorine-containing protoporphyrin derivative of formula (I):

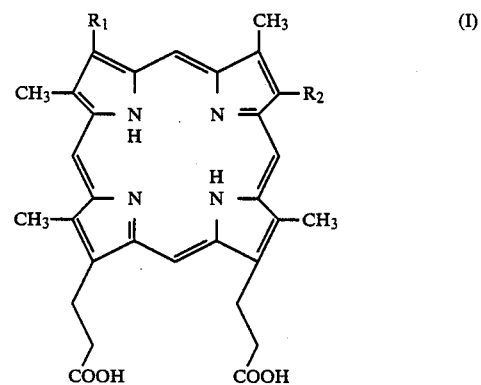

wherein $R_1$ and $R_2$ each independently is $-CH=CH_2$ or $-CH=CF_2$ with the proviso that $R_1$ and $R_2$ cannot both be $-CH=CH_2$; and salts thereof.

They have remarkable property of peculiarly concentrating or accumulating in the cancer tissues, and very useful as a diagnostic agent of minute cancer in a NMR diagnosis method.

4 Claims, 1 Drawing Sheet

FLUORINE-CONTAINING PROTOPORPHYRIN DERIVATIVES AND THEIR SALTS

BACKGROUND OF THE INVENTION (1) Field of the Invention

This invention relates to a fluorine-containing protoporphyrin derivative and its salts which are useful as a diagnostic agent in the early detection of minute cancer.

(2) Description of the Background Art

Many reports have been published which indicate that porphyrins are prone to concentrate in cancerous tissues.

On the other hand, recent technical advances have made it possible to lase tissues in the living body by use of glass fibers. A so-called photodynamictherapy, an application of this technique, has now been attracting a lot of attention, where a subject is administered porphyrins which have a marked tendency to concentrate or accumulate in cancerous tissues, then subjected to laser light which is absorbed by the porphyrins and in turn the cancerous tissues are destroyed.

The principle of photodynamic therapy is that upon receiving laser beams, atoms constituting porphyrins are excited to produce activated oxygens which attack the cancerous cells to extinguish them. Since porphyrins concentrated or accumulated in the cancerous tissues emit red fluorescence upon receiving beams in the vicinity of 400 nm, they are expected to be useful in the cancer diagnosis as well as the cancer treatment. Today, active researches are being made on the diagnosis and treatment using hematoporphyrin derivatives. However, since the hematoporphyrin derivatives currently in use are a mixture of various porphyrin derivatives, they have potential problems to meet the medicinal purposes. Therefore, they have not yet been put into practical use.

Besides, in order to make the photodynamic therapy practical and further utilize it in cancer treatments, improvement is called for as to the following disadvantages. First, the diagnosis and the treatment are limited to the region where glass fibers can reach. Second, even though the cancerous region is reached by the fibers, laser irradiation is useful only on cancer in situ, and cannot reach deeper cancer tissues. In such case, no treatment nor diagnosis are possible by this method.

As mentioned above, it is considered that there are limitations in detecting cancers by the laser irradiation using porphyrins.

In the modern medical field, there are proposed a variety of surgical and internal treatments including radiotherapy to cure cancer diseases. It is said that if we can detect cancers in their early stages, the curing ratio should be greatly improved.

We cannot overemphasize the importance of the early detection of minute cancer including precancerous regions. The early diagnosis is one of the most important subject matters in the modern cancer treatments.

Meanwhile, diagnosis of various diseases by NMR (nuclear magnetic resonance) has recently received a lot of attention due to the advantage in that the internal organs of the living body can be observed as they are without being affected. Especially, being coupled with the recent rapid progress in the development of superconductive magnets, the NMR diagnosis is expected to be a future diagnosis of many diseases.

Presently, NMR has been used to detect $^1H$ nuclei in the living body. However, since the nuclei of $^1H$ are present in water which occupies most of the living body, no minute configurations other than gross shapes of internal organs can be observed, and therefore, the detection of minute cancer is thought to be impossible. As the nuclear species capable of detecting NMR spectrums, $^{13}C$, $^{15}N$, $^{31}P$, $^{19}F$, etc. may be mentioned other than $^1H$. Among these, $^{13}C$ and $^{31}P$ are thought to give almost the same resolution as $^1H$ since they are also present in the living body.

SUMMARY OF THE INVENTION

The present inventors, therefore, focused on the use of $^{19}F$ which are scarcely present in the living body among the nuclear species capable of detecting NMR, and attempted to introduce fluorine into porphyrin derivatives. In other words, their idea was that when porphyrins containing fluorine were administered to a patient, and if they could be concentrated or accumulated in the cancer tissues, NMR data with considerably less background than other nuclear species could b obtained, leading to the early diagnosis of minute cancer. This invention was achieved based on the above idea and findings.

Accordingly, an object of the invention is to provide fluorine-containing protoporphyrin derivatives of formula (I) and their salts:

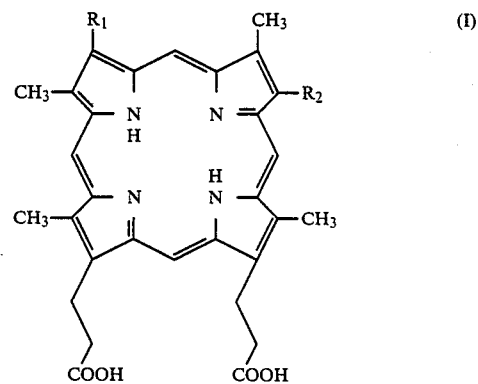

wherein $R_1$ and $R_2$ each independently is $-CH=CH_2$ or $-CH=CF_2$ with the proviso that $R_1$ and $R_2$ cannot both be $-CH=CH_2$, which compounds are remarkable in the property of peculiarly concentrating or accumulating in the cancer tissues, thus very useful as a diagnostic agent of minute cancer.

DETAILED DESCRIPTION OF THE INVENTION AND PREFERRED EMBODIMENTS

Figure 1:
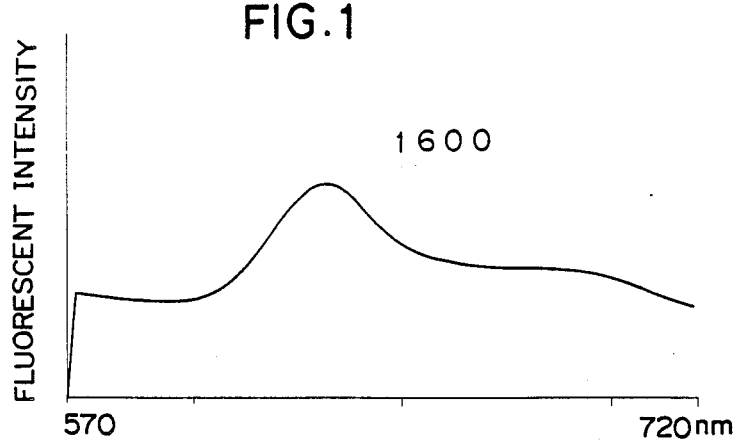
FIG. 1 shows fluorescent intensity for the cancerous tissue measured in the test using a mouse (Example 3).

The fluorine-containing protoporphyrin derivatives (I) of this invention can be prepared according to the following reaction sequence:

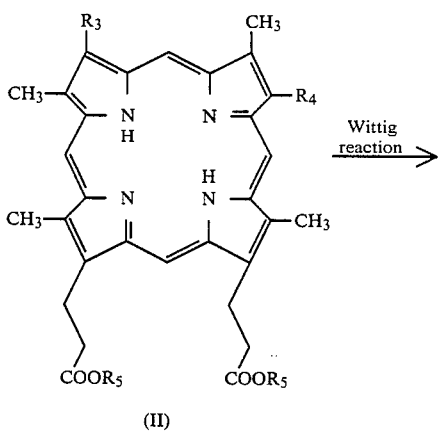

(II)

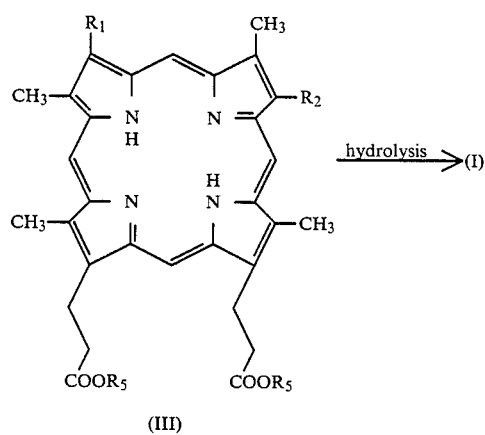

(III)

wherein $R_3$ and $R_4$ each independently is formyl or —CH=CH$_2$ with the proviso that $R_3$ and $R_4$ cannot both be —CH=CH$_2$, $R_5$ is an ester residue, and $R_1$ and $R_2$ are as defined before.

In other words, the compounds (I) or their salts of this invention can be prepared by the first step where a protoporphyrin ester derivative (II) (hereinafter referred to as an aldehyde) which has a formyl group at either 3 or 8 position or at both positions is subjected to the Wittig reaction to convert formyl into difluorovinyl, followed by the second step where the obtained protoporphyrin ester derivative (III) (hereinafter referred to as a difluorovinylester) having difluorovinyl is subjected to hydrolysis.

The aldehyde (II) can be obtained according to H. H. Inhoffen et al., Justus Liebigs Ann. Chem. 730, 173 (1969), which process starts from protoporphyrin ester followed by photo-oxidation or oxidation by periodic acid, osmium tetroxide, etc.

The reaction which converts aldehyde (II) into difluorovinyl-ester (III) is the Wittig reaction, where the aldehyde (II), sodium difluoromonochloroacetate and triphenylphosphine are mixed and heated at temperatures ranging from 100° to 200° C. over 30 minutes to 10 hours.

The obtained difluorovinyl-ester (III) is subjected to hydrolysis in a solvent such as toluene along with a base such as sodium hydroxide.

The compounds (I) of this invention, especially sodium $3^2$- difluorovinylprotoporphyrin, are useful for the early detection of minute cancer in a NMR diagnosis method due to their characteristic property of selectively accumulating in the cancer tissues when administered in the living body. The compound (I) of the present invention can be applied to early detection of various cancers, e.g. those in digestive organs, lung, etc. It is particularly useful for early detection of stomach cancer and lung cancer.

The compound may be administered either orally or by injection. A preferable dose for oral administration is 100 to 1,000 mg, with particularly preferable range being 300 to 500 mg. When it is injected, a dose may be 30 to 500 mg, and preferably 100 to 300 mg. It is desirable that the compound be administered about 24 hours before NMR diagnosis. A preferable concentration of the compound in injection liquied is about 1 to 30 mg/ml.

This invention is now explained by way of examples, which should not be construed as limiting the invention thereto.

EXAMPLE 1

(1) Synthesis of $3^2$-difluorovinylprotoporphyrin (3-FPP) dimethyl ester 70 mg of spirographis porphyrindimethyl ester (3-aldehyde) and 786 mg of triphenylphosphine were placed in a 50 ml 2-neck flask provided with a Dimroth. After the air in the flask was purged and replaced with argon, 10 ml of N-methyl-2-pyrrolidine (NMP) was added and the flask was heated at 160° C., to which a NMP (7 ml) solution of 456 mg sodium difluoromonochloroacetate was added over 47 minutes. After the 30 minute reaction at that temperature, the flask was cooled down. The reaction solution was poured into ice water to complete the reaction. From the obtained aqueous solution, a reaction product was extracted with methylene chloride. The extract was washed with water, then the methylene chloride layer was dried over magnesium sulfate, and the methylene chloride was distilled off under reduced pressure to obtain a reaction product. The product was purified by silica gel column chromatography to obtain 31 mg of 3-FPP dimethyl ester (yield: 42%).

Melting Point: 203.5°–205.5° C.

IR(KBr) cm$^{-1}$:3324 (N-H), 1738 (ester carbonyl), 1198, 1176 (C—F)

$^1$H-NMR (400 MHz, CDCl$_3$) ppm: 9.99 (s), 9.89 (s), 9.87 (s), 9.66 (s) (—CH=), 8.18 (dd, Ha, Jab=11 Hz, Jac 17 Hz), 6.47 (d, Hd, Jab'=25 Hz), 6.33 (dd, Hc, Jbc=1.4 Hz, Jac=17 Hz), 6.17 (dd, Hb, Jbc=1.4 Hz, Jab=11 Hz), 4.45 (m) (—CH$_2$), 3.66 (s), 3.65 (s), 3.55 (s), 3.52 (s), 3.46 (d, J=2.4 Hz), 3.23 (m) (—CH$_2$), ——4.09 (b) (=NH)

$^{19}$F-NMR (90 MHz, CDCl$_3$, CFCl$_3$) ppm: −82.14 (dd, Fb', Jb'd=25 Hz, Ja'b'=26 Hz), −83.76 (d, Fa', Ja'b'=26 Hz)

MS: m/e=626 (M+)

High MS: Obsd 626.27017

C$_{36}$H$_{36}$N$_4$O$_4$F$_2$: Error, 0.1

(2) Synthesis of 8-FPP dimethyl ester 70 mg of isospirographis porphyrindimethyl ester (8-aldehyde) and 746 mg of triphenylphosphine were placed in a 50 ml 2-neck flask provided with a Dimroth. After the air in the flask was purged and replaced with argon, 10 ml of NMP was added and the flask was heated at 160° C., to which a NMP (7 ml) solution of 436 mg sodium difluoromonochloroacetate was added over 47 minutes. After the 30 minute reaction at that temparature, the flask was cooled down. The reaction solution was poured into ice water to complete the reaction. From the obtained aqueous solution, a reaction product was extracted with methylene chloride. The extract was washed with water, then methylene chloride layer was dried over magnesium sulfate, and the methylene chloride was distilled off under reduced pressure to obtain a reaction product. The product was purified by silica gel column chromatography to obtain 41 mg of 8-FPP dimethyl ester (yield: 55%).

Melting point 204°-205.5° C.
IR(KBr) cm$^{-1}$:3324 (N—H), 1738 (ester carbonyl), 1194, 1170 (C—F)
$^1$H—NMR (400 MHz, CDCl$_3$) ppm: 9.98 (s), 9.87 (s), 9.85 (s), 9.63 (s) (—CH=), 8.17 (dd, Ha, Jab=11 Hz, Jac=16 Hz), 6.44 (d, Hd, Jda'=25 Hz), 6.32 (d, Hc, Jab=16 Hz), 6.16 (d, Hb, Jab=11 Hz), 4.31 (m) (—CH$_2$—), 3.66 (s), 3.65 (s), 3.55 (s), 3.54 (s), 3.51 (s), 3.45 (d, J=2.4 Hz), 3.23 (m)(—CH$_2$—), −4.1 (b) (=NH)
$^{19}$F-NMR (90 MHz, CDCl$_3$, CFCl$_3$), ppm: −82.02 (dd, F'b, Jdb'=25 Hz, Ja'b'=26 Hz), −83.64 (d, Fa', Ja'b'=26 Hz)
MS: m/e=626 (M+)
High MS: obsd, 626.27017
C$_{36}$H$_{36}$N$_4$O$_4$F$_2$: Error, 0.2

(3) Synthesis of 3,8-FPP dimethyl ester 40 mg of 3,8-dialdehyde and 788 mg of triphenylphosphine were placed in a 50 ml 2-neck flask provided with a Dimroth. After the air in the flask was purged and replaced with argon, 10 ml of NMP was added and the flask was heated at 160° C., to which a NMP (7 ml) solution of 455 mg sodium difluoromonochloroacetate was added over 15 minutes. After the 30 minute reaction at that temperature, the flask was cooled down. The reaction solution was poured into ice water to complete the reaction. From the obtained aqueous solution, a reaction product was extracted with methylene chloride. The extract was washed with water, then methylene chloride layer was dried over magnesium sulfate, and the methylene chloride was distilled off under reduced pressure to obtain a reaction product. The product was purified by silica gel column chromatography to obtain 18 mg of 3,8-FPP dimethyl ester (yield: 40%).

Melting point: 212°-219.5° C.
IR(KBr) cm$^{-1}$:3324 (N-H), 1736 (estercarbonyl), 1198, 1172 (C-F)
$^1$H-NMR (90 MHz, CDCl$_3$) ppm: 9.92 (2H, s), 9.76 (2H, s)(—CH=), 6.55 (d, 2H, Jab'=26 Hz), 4.33 (dd, 4H, J=7 Hz, J'=7 Hz)(—CH$_2$—), 3.66 (s, 6H), 3.54 (s, 6H), 3.48 (s, 6H), 3.24 (dd, 4H, J=7 Hz, J'=7 Hz)
$^{19}$F-NMR(CDCl$_3$, CFCl$_3$) ppm: −81.86 (dd, Fb', Jab'=26HZ, Ja'b'=26 Hz), −83.38 (d, Fa', Ja'b'=26 Hz)
MS: m/e=662 (M+)
High MS: Obsd, 662.25228
C$_{36}$H$_{34}$N$_4$O$_4$F$_4$: Error, 0.7

Example 2

(1) Hydrolysis of 3-FPP dimethyl ester 14.3 mg of 3-FPP dimethyl ester was dissolved in 10 ml of toluene, to which 0.1 ml methanol solution of 1.8 mg sodium hydroxide was added. After one hour reflux, the flask was left to cool down. Black crystals were collected by filtration, dried under reduced pressure to obtain 12.4 mg disodium of 3-FPP (3-FPPN). 1 mg of this sodium salt was dissolved in 1 ml of methanol hydrochloride (1–10), heated at 60° C. over 30 minutes followed by being left to cool down. The system was neutralized by ammonium carbonate and extracted with methylene chloride. Analysis of the extract by thin layer chromatography revealed a spot at the Rf value identical to 3-FPP dimethyl ester. No other spots were observed.

(2) Hydrolysis of 8-FPP dimethyl ester 14.2 mg of 8-FPP dimethyl ester was dissolved in 10 ml of toluene, to which 0.1 ml methanol solution of 1.8 mg sodium hydroxide was added. After one hour reflux, the flask was left to cool down. Black crystals were collected by filtration, dried under reduced pressure to obtain 13.1 mg disodium of 8-FPP (8-FPPN). 1 mg of this sodium salt was taken and dissolved in 1 ml of methanol hydrochloride (1–10), heated at 60° C. over 30 minutes followed by being left to cool down. The system was neutralized by ammonium carbonate and extracted with methylene chloride. Analysis of the extract by thin layer chromatography revealed a spot at the Rf value identical to 8-FPP dimethyl ester. No other spots were observed.

(3) Hydrolysis of 3,8-FPP dimethyl ester 16.9 mg of 3,8-FPP dimethyl ester was dissolved in 10 ml of toluene, to which 0.1 ml methanol solution of 2.1 mg sodium hydroxide was added. After one hour reflux, the flask was left to cool down. Black crystals were collected by filtration, dried under reduced pressure to obtain 15.1 mg disodium of 3,8-FPP (3,8-FPPN). 1 mg of this sodium salt was taken and dissolved in 1 ml of methanol hydrochloride (1–10), heated at 60° C. over 30 minutes followed by being left to cool down. The system was neutralized by ammonium carbonate and extracted with methylene chloride. Analysis of the extract by thin layer chromatography revealed a spot at the Rf value identical to 3,8-FPP dimethyl ester. No other spots were observed.

EXAMPLE 3

A nude mouse which was transplanted with a human stomach cancer (MKN-45) was intraperitoneally administered with 1.25 mg of test liquid which was prepared by dissolving 2 mg of 3-FPPN in 2 mg of isotonic sodium chloride solution. 24 hours after the administration, the mouse was cut up and the cancerous tissue, the liver and the stomach were taken for immediate freezing.

Figure 2:
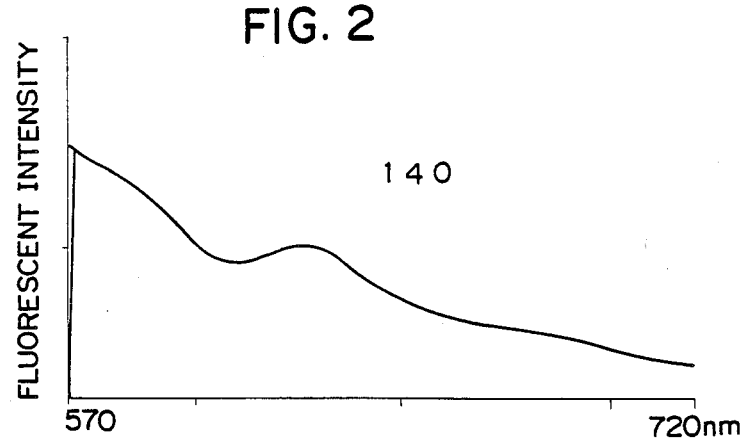
FIG. 2 shows fluorescent intensity for the liver tissue measured in the test using a mouse (Example 3).
Figure 3:
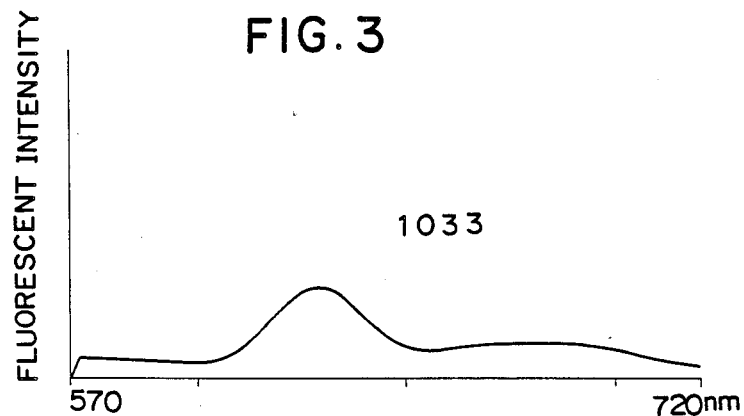
FIG. 3 shows fluorescent intensity for the stomach tissue measured in the test using a mouse (Example 3).

These samples were freeze-dried, then ground in a mortar. 25 mg of each sample was added with 75 μl of distilled water, mixed well over 30 minutes. 900 μl of methanol containing 2% diisoproppylamine was further added for 30 minute blending. An extract was centrifuged at 3000 rpm for 20 minutes to obtain 100 μl of supernatant, to which 900 μl of methanol was added. Fluorescent spectrum at the excitation wave length of 400 nm was measured in the range from 570 nm to 720 nm. The results are shown in FIGS. 1 to 3. As shown in the figures, fluorescent intensities measured at 630 nm corresponding to porphyrins were 1600 for the cancerous tissue, 140 for the liver tissue and 1033 for the stomach tissue, respectively.

From the data, it is concluded that 3-FPPN was selectively accumulated or concentrated in the cancerous tissue.

Since mice are well taken as a model animal in the art, application to mammals including human would be apparent.

What is claimed is:

1. A fluorine-containing protoporphyrin derivative of formula (I):

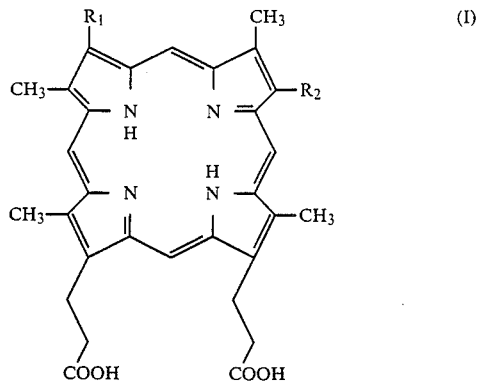

wherein $R_1$ and $R_2$ each independently is $-CH=CH_2$ or $-CH=CF_2$ with the proviso that $R_1$ and $R_2$ cannot both be $-CH=CH_2$; and salts thereof.

2. The fluorine-containing protoporphyrin derivative and salts thereof according to claim 1, wherein $R_1$ is $-CH=CH_2$ and $R_2$ is $-CH=CF_2$.

3. The fluorine-containing protoporphyrin derivative and salts thereof according to claim 1, wherein $R_1$ is $-CH=CF_2$ and $R_2$ is $-CH=CH_2$.

4. The fluorine-containing protoporphyrin derivative and salts thereof according to claim 1, wherein both $R_1$ and $R_2$ are $-CH=CF_2$.

* * * * *